(12) United States Patent
Hobbs et al.

(10) Patent No.: US 8,231,603 B2
(45) Date of Patent: Jul. 31, 2012

(54) IRREVERSIBLE ELECTROPORATION AND TISSUE REGENERATION

(75) Inventors: Eamonn P. Hobbs, Queensbury, NY (US); James G. Lovewell, San Leandro, CA (US); Robert M. Pearson, San Jose, CA (US)

(73) Assignee: AngioDynamics, Inc., Latham, NY (US)

(*) Notice: Subject to any disclaimer, the term of this patent is extended or adjusted under 35 U.S.C. 154(b) by 299 days.

(21) Appl. No.: 12/703,355

(22) Filed: Feb. 10, 2010

(65) Prior Publication Data

US 2010/0204638 A1   Aug. 12, 2010

Related U.S. Application Data

(60) Provisional application No. 61/151,305, filed on Feb. 10, 2009.

(51) Int. Cl.
*A61M 31/00* (2006.01)

(52) U.S. Cl. ........ 604/522; 604/506; 604/507; 604/511; 606/41

(58) Field of Classification Search ............... 604/20–21, 604/522, 501, 506–507, 511; 606/41, 32
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss et al. |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |

(Continued)

FOREIGN PATENT DOCUMENTS

DE    863111    1/1953

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Theodore Stigell
(74) *Attorney, Agent, or Firm* — Tara L. Clothier

(57) ABSTRACT

A method and device are herein described to treat a target region of tissue, using at least one energy delivery device coupled to a power source and positioned in a treatment position so as to irreversibly electroporate tissue to ablate a target region, and introduce regenerative materials into a treated region.

21 Claims, 14 Drawing Sheets

U.S. PATENT DOCUMENTS

| | | |
|---|---|---|
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,807,395 A * | 9/1998 | Mulier et al. .................. 606/41 |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Nanda et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 7,565,208 B2 * | 7/2009 | Harris et al. .................. 607/116 |
| 8,109,926 B2 * | 2/2012 | Azure .................. 606/41 |
| 2001/0044596 A1 | 11/2001 | Jaafar |
| 2002/0010491 A1 | 1/2002 | Schoenbach |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088189 A1 | 5/2003 | Tu et al. |
| 2003/0105454 A1 | 6/2003 | Cucin |
| 2003/0130711 A1 | 7/2003 | Pearson et al. |
| 2003/0170898 A1 | 9/2003 | Gundersen et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0243107 A1 | 12/2004 | Macoviak |
| 2004/0267189 A1 | 12/2004 | Mavor et al. |
| 2005/0010259 A1 | 1/2005 | Gerber |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0043345 A1 | 2/2007 | Davalos et al. |
| 2007/0093789 A1 | 4/2007 | Smith |
| 2007/0118069 A1 | 5/2007 | Persson et al. |
| 2008/0052786 A1 | 2/2008 | Lin et al. |
| 2008/0269838 A1 | 10/2008 | Brighton |
| 2009/0269317 A1 | 10/2009 | Davalos |
| 2009/0281477 A1 * | 11/2009 | Mikus et al. .................. 604/21 |
| 2010/0030211 A1 | 2/2010 | Davalos et al. |

FOREIGN PATENT DOCUMENTS

| | | |
|---|---|---|
| DE | 4000893 | 7/1991 |
| EP | 0378132 | 7/1990 |
| EP | 0935482 | 5/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |
| WO | WO2009134876 | 11/2009 |

OTHER PUBLICATIONS

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition.

PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Brown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, *Newsweek*, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al ., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology* XII, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Foster, R.S., et al., High-intensity focused ultrasound in the treatment of prostatic disease. *Eur. Urol.*, 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Precision Office TUNA System, When Patient Satisfaction is Your Goal.

Rols, M.P., et al., Highly Efficient Transfection of Mammalian Cells by Electric Field Pulses: Application to Large Volumes of Cell Culture by Using a Flow System, *Eur. J. Biochem*. 1992, 206, pp. 115-121.

Rubinsky, B., ed, Cryosurgery. *Annu Rev. Biomed.* Eng. vol. 2 2000. 157-187.

Schmukler, Impedance Spectroscopy of Biological Cells, downloaded from IEEE Xplore website.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

TUNA—Suggested Local Anesthesia Guidelines.

Vidamed, Inc., Transurethral Needle Ablation (TUNA): Highlights from Worldwide Clinical Studies, Vidamed's Office TUNA System.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

The International Search Report in PCT/US10/23752 which was mailed on Jan. 3, 2011.

* cited by examiner

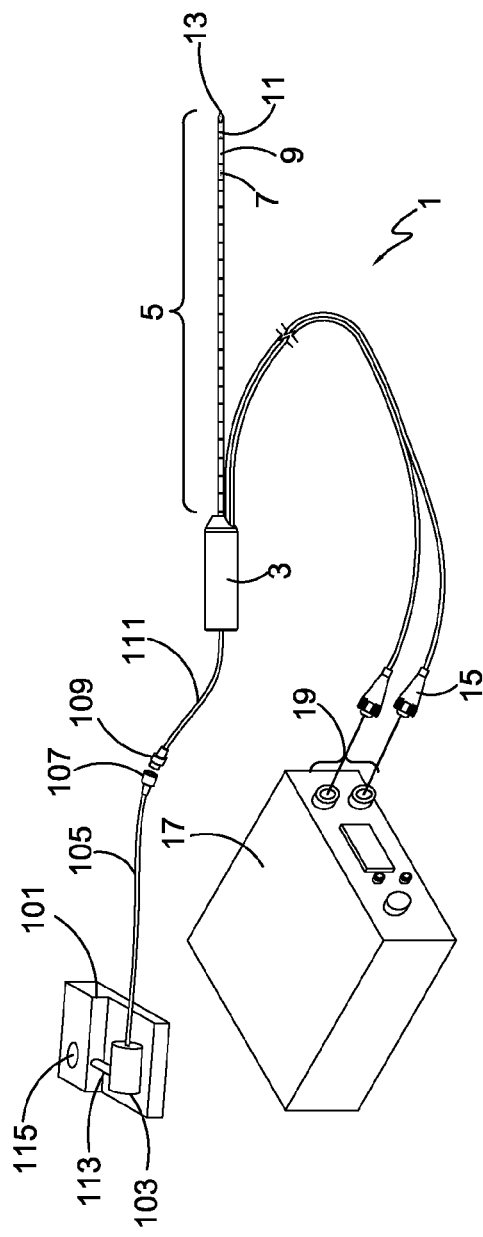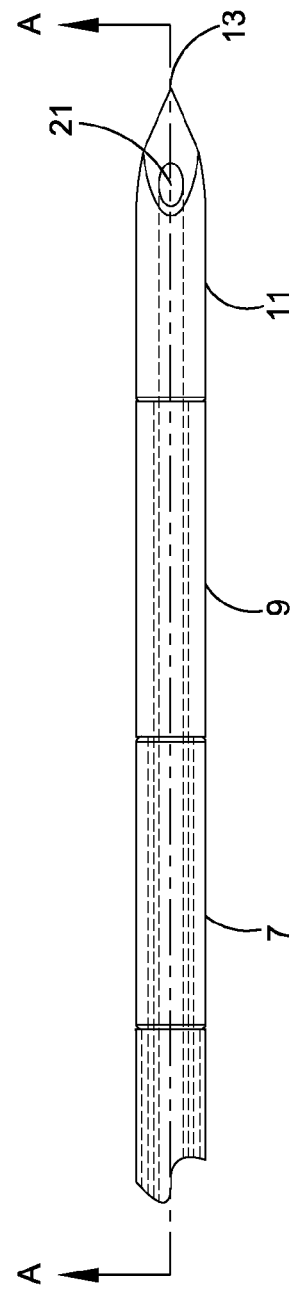
FIG. 1A
FIG. 1B

IRREVERSIBLE ELECTROPORATION AND TISSUE REGENERATION

CROSS REFERENCE TO RELATED APPLICATIONS

This application claims priority to U.S. Provisional Application Ser. No. 61/151,305, Irreversible Electroporation and Tissue Regeneration, filed Feb. 10, 2009, which is incorporated herein by reference.

BACKGROUND OF THE INVENTION

1. Field of the Invention

The present invention relates generally to advancements in medical treatment. More specifically, this present invention is related to effectively treating a target region of tissue with Irreversible Electroporation (IRE), followed by introduction of regenerative materials leading to regrowth, restructuring, and cellular repopulation of the treated region.

2. Description of the Related Art

Tissue ablation is a medically necessary activity with destructive effects leading to cellular death within a target region (also herein called target tissue). Historically this endeavor has included a series of methods, each with varying degrees of effectiveness and subsequent levels of unintended consequences including adverse effects to surrounding tissue. Depending on the method used for tissue ablation and any underlying pathophysiology related to the medical treatment, the patient may have remaining tissue that is damaged, disorganized, and in need of repair. This is due to the fact that ablation techniques used historically have been nonselective in that they mediate cell death with methods such as extreme heat or cold. These methods will non-selectively and adversely affect blood vessels, nerves, and connective structures adjacent to the ablation zone. Disruption of the nerves locally impedes the body's natural ability to sense and regulate homeostatic and repair processes at and surrounding the ablation region. Disruption of the blood vessels prevents removal of debris and detritus. This also prevents or impedes repair systems, prevents homing of immune system components, and generally prevents normal blood flow that could carry factors such as hormones to the area. Without the advantage of a steady introduction of new materials to a damaged area, reconstruction of the blood vessels and internal linings become retarded as redeployment of cellular materials is inefficient or even impossible. Therefore historical ablation treatments do not leave tissue in an optimal state for self-repair in regenerating the region.

Recent developments offer an opportunity to advance the regenerative process following ablation treatments. A recent development in tissue ablation involves the use of irreversible electroporation (IRE). IRE offers the advantage of being a nonthermal ablation technique, which avoids some of the adverse consequences associated with temperature changes of ablative techniques such as radiofrequency (RF) ablation, microwave ablation, or even cryoablation. In addition, IRE has been shown to have sparing effects on structural components, leaving blood vessels and connective structures intact. This provides the advantage of providing a scaffold system which could then be utilized to increase the rate of reconstruction in the rebuilding process of recovery following ablation.

IRE has been applied to the treatment of tissue using ablation, and this technology has the distinct advantage of inducing cell necrosis without raising the temperature of the ablation zone. More specifically IRE is a technology where electrical pulses in the range of nanoseconds to milliseconds are applied to tissue to produce cellular necrosis and irreversible cell membrane permeabilization. More precisely, IRE treatment acts by creating defects in the cell membrane that are nanoscale in size and that lead to a disruption of homeostasis while sparing connective and scaffolding structure and tissue. These points have been addressed in the following publications, which are hereby incorporated by reference: Lavee J. *A Novel Nonthermal Energy Source for Surgical Epicardial Atrial Ablation: Irreversible Electroporation*. The Heart Surgery Forum. Vol. 10(2):96-101 (2007), and U.S. Patent Application Publication Number US 20060293731 A1, "Methods and systems for treating tumors using electroporation," application Ser. No. 11/165,961 filed on Jun. 24, 2005.

A distinct advantage of the IRE technology is the sparing of surrounding tissue, and in fact the structure of surrounding bile ducts, blood vessels, and connective tissue remains intact following application of IRE. This technology has been described in the following two patent application publications which are hereby incorporated by reference: Patent Application Publication Number WO2005/06284A2, "Tissue Ablation with Irreversible Electroporation," as well as U.S. Patent Application Publication Number US 2007/0043345A1, "Tissue Ablation with Irreversible Electroporation," application Ser. No. 10/571,162.

By utilizing IRE in combination with advanced regenerative technologies, there exists a vast potential for regrowth, regeneration, and cellular repopulation in a treated region that far surpasses current treatment modalities. The reason for this starts with the fact that the IRE treatment leaves structures such as blood vessels and nerves intact and ends with the fact that there are technologies that can take advantage of that fact for increased regeneration capabilities. Specifically, the remaining vessels and connective tissues are structures that provide a scaffold that can be built upon. These vessels can also act as a conduit for new materials, while remaining nerves can act to assist monitoring and mediating of the local conditions. Meanwhile, the introduction of regenerative materials to these locations can take advantage of the remaining foundation to advance regeneration. One example of a component of regenerative materials that would work synergistically with the IRE technology would be stem cells.

Effective development and use of stem cells is also a relatively recent development and is an emerging branch of technology that offers vast potential for enhancing regenerative capacity for an organ or tissue. A stem cell can be defined as a cell capable of producing unaltered daughter cells continuously, and a cell that is also capable of producing daughter cells that have differentiated characteristics. In other words, stem cells producing progeny that are to have separate or distinguished fates will have undergone asymmetric division while those daughter cells having the same fate have undergone symmetric division.

These concepts have been described in the following two papers, hereby incorporated by reference:

Smith A., *A Glossary for Stem Cell Biology*. Nature Vol. 441(7097):1060-61 (2006).

Morrison S. J., Kimble J., *Asymmetric and Symmetric Stem Cell Divisions in Development and Cancer*, 441(7097) Nature 1068, 1068-74 (2006).

One advantage of utilizing stem cells in a regenerative process involves the ability of a small number of cells to repopulate an area since the dividing cells have less potential for exhaustion on division. In fact, there are a variety of stem cell categories, which can be grossly broken into totipotent, pluripotent, multipotent, and unipotent, which are indicated here with respective decreasing plasticity or potency. A second advantage of utilizing stem cells is that the cells can differentiate into one or more cell types depending on the milieu of factors in the host niche environment. The power of this capacity can potentially be utilized as an astounding regenerative tool of medicine that could combat tissue injury, lead to treatments for degenerative diseases, and the normal decline of aging. This concept has been addressed in the following two papers, hereby incorporated by reference:

Rando T. A. *Stem Cells, Ageing and the Quest for Immortality*. Nature. Vol. 441(7097):1080-1086 (2006).
Ioannidou E., *Therapeutic modulation of growth factors and cytokines in regenerative medicine*, 12(19) Current Pharmaceutical Design. Vol. 12(19):2397 (2006).

Stem cells could also be used for therapies for progressive blindness, neurological disorders including stroke, Parkinson's disease, and multiple sclerosis, and also holds potential for treatment of heart disease. This concept has been discussed in the following three papers, hereby incorporated by reference:

Lindvall O., Kokaia Z., *Stem cells for the treatment of neurological disorders*. Nature. Vol. 441(7097): 1094-1096 (2006).
Couzin J., *A Shot of Bone Marrow Can Help the Heart*. Science. Vol 313: 1715-1716 (2006).
Srivastava D., Ivey K. N., *Potential of Stem-Cell-Based Therapies for Heart Disease*. Nature. Vol. 441(7097): 1097-1099 (2006).

This invention allows for the combined use of nonthermal ablation of undesired tissue through IRE with the introduction of regenerative materials that will allow the regrowth of tissue following ablation. A need exists for an apparatus and method for accomplishing effective ablation followed by introduction of regenerative materials so as to increase the rate of regrowth, the rate of reconstruction, and cellular repopulation of a region following ablation. There is a need for a method and device that can ultimately decrease patient recovery times in a significant number of different treatment situations through more effective regeneration. The proposed method and apparatus matches these needs and allows for an increased opportunity for regrowth in tissues through the introduction of regenerative materials that may include stem cells. The proposed method and apparatus also provides for a treatment that can be used widely; in tissues that naturally regenerate (to enhance the effectiveness and rate of regeneration), in tissues without significant natural regenerative powers, and in those with pathophysiological factors that may otherwise impede regenerations.

Applicant(s) believe(s) that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

BRIEF SUMMARY OF THE INVENTION

The present invention provides among other things a method and apparatus to advance medical treatment outcomes through the utilization of regenerative therapies following targeted nonthermal tissue ablation to return tissue of a treated region more rapidly and effectively to a non-pathological, normal, homeostatic state.

There exists a need in the art for a method and apparatus capable of providing a framework for tissue regeneration following the use of nonthermal tissue ablation such as IRE which effectively spares structural components leaving a structure upon which regeneration can be initiated. Nonthermal IRE ablation involves ablation where the primary method of cellular disruption leading to death is mediated via electroporation (rather than factors such as effects of or responses to heating). In certain embodiments, depending on the parameters mentioned (including time that the resulting temperature occurs), cellular death can be mediated via nonthermal IRE up to approximately 50° C. A parameter can also be a voltage, amperage, pulse number, timing of pulses, or duration between pulses, or a combination of at least one of voltage, amperage, pulse number, timing of pulses, or duration between pulses.

There exists a need in the art for a device and method that can provide ablative and regenerative therapies in a single method or apparatus, or in a simplified series of effective applications of regenerative materials so as to increase the effectiveness of treatments, provide components for cellular rebuilding and introduce factors inducing proliferative response and regrowth to advance objectives for patient recovery. Provided herein is a method and device for treating tissue wherein the device has a channel for release of materials or factors in a device also capable of electroporation.

The above and other purposes may be achieved using a method to nonthermally ablate tissue using irreversible electroporation and to introduce regenerative materials into the ablated area. This method provides, among other things, a patient with a potentially decreased recovery time through increased efficiency of tissue regrowth and reformation. Regenerative materials can be released through the same probe (or same device) that is used in ablation, thus leading to ablation directly followed by introduction of regenerative materials. Regenerative materials can also be released using a separate device such as syringe or second probe.

The above and other purposes may be achieved using regenerative materials of various qualities: those that are totipotent, pluripotent, multipotent, and unipotent (cells), as well as those that are autogeneic, isogeneic, allogeneic, and xenogeneic. Regenerative materials can also include a variety of cells obtained through a variety of mechanism, including: embryonic stem cells, adult stem cells, vascular endothelial cell precursors and mesodermal stromal cells. These cells may be obtained from the use of magnetic beads, optical sensors, electric fields, as well as dielectrophoresis. Cells within the regenerative materials also may have a variety of distinct markers, protein expressions, or genetic compositions. This variety allows for multiple purposes to be effectively met.

There exists a need in the art for an invention that can provide ablative and regenerative therapies in a single method or apparatus and that can be used in a wide variety of procedures. This purpose may be achieved using irreversible electroporation, a nonthermal ablation method and by introducing regenerative materials; which can be applied in percutaneous, laparoscopic, and open surgery procedures. The method can be used when the target tissue either actually is one of the following tissues or is within the following tissues: digestive, skeletal, muscular, nervous, endocrine, circulatory, reproductive, integumentary, lymphatic, urinary, and soft tissue. The method can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, or tumorous.

The above and other purposes may be achieved by applying materials subsequent to ablation that will enhance the regenerative properties of remaining tissue. Once power has been used to lead to the effect of irreversible electroporation in a target region, the remaining tissue, that is still a target region (just in a different state of physiology or viability) may also be called a treated region. This treated region can then be altered so as to bring about regeneration of that remaining tissue. This can involve direct application of regenerative materials, or can first involve a release of factors to rebalance any altered conditions as a result of the ablation. These materials and factors may include singly and in combination VEGF, cytokines, and anti-inflammatory agents, water, ions, hormones, paracrine agents, pharmacological mediators and vasoreactive elements. To ensure complete regeneration, the materials may need to be applied acutely or chronically, from one time to many times. In various embodiments, regenerative materials such as stem cells are released at any given time in the ablation therapy, from multiple sources singly or in combination and simultaneously or nonsimultaneously.

The above and other purposes may be achieved by applying regenerative materials that can be used to reestablish normal linings and membranes and cellular networks. This can involve direct application of a variety of regenerative materials released singly or in combination, in whole, in part, or precursors of DNA, RNA, proteins, carbohydrates, sugars, lipids, enzymes, proteases, steroids, amino acids, purine bases, pyrimidine bases, deoxyribose sugar, ribose sugar, nucleosides, adenosine-triphosphate, and adenosine biphosphate, polysaccharides, proteoglycans, hyaluronic acid, collagen, fibronectin, elastin, laminin, and integrins. The regenerative material could also include singly or in combination smooth muscle cells, epithelial cells, endothelial cells, liver cells, lung cells, pancreatic cells, and bone cells. In embodiments where the regenerative materials that are applied include cells, at least one cell can be the same cell type as the primary cell type of the target region. The primary cell type would refer either to the most predominant cell in number or area or the cell type providing that area with its anatomical name (such as a liver cell in a liver).

The above and other purposes may be achieved through the use of a device that applies nonthermal irreversible electroporation and that is capable of releasing regenerative materials to the ablation site.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

FIG. 1A depicts a perspective view of an IRE power source coupled to an energy delivery device that in this depiction is a bipolar probe utilized in the current invention. Also shown is a container for regenerative materials and an infusion pump for movement of materials.

FIG. 1B depicts an enlarged side-view of the distal portion of the shaft of the bipolar probe. In FIG. 1B the shaft is shown as one example of a shaft, particularly a needle.

Figure 1C:
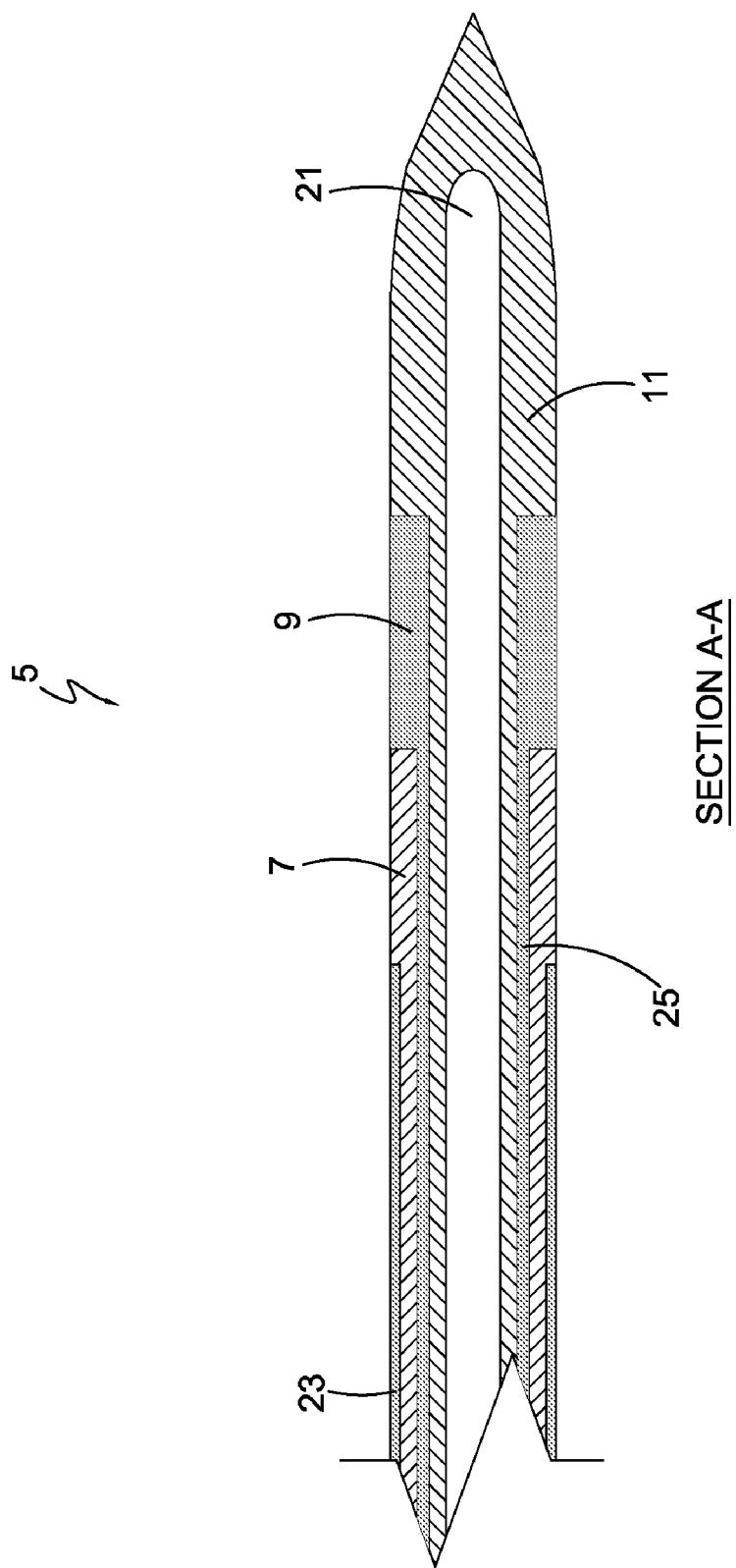
FIG. 1C depicts an enlarged cross-sectional view of a portion of the needle of the bipolar probe utilized in the current invention.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. The full scope of the inventions is not limited to the examples that are described below. FIGS. 1-9 demonstrate utilization of the ablation and regenerative method and apparatus in a vessel and a target tissue within a liver and within a lung, and these are simply representative. Target regions can include or be within digestive, skeletal, muscular, nervous, endocrine, circulatory, reproductive, integumentary, lymphatic, urinary, and soft tissue. The targets may also include benign or malignant, cancerous, neoplastic, preneoplastic, or tumors as stand-alone targets or targets found within another tissue (such as an organ or organ system). Ablation can be performed in each of laparoscopic, percutaneous, and open surgical procedures.

Regeneration refers to at least a partial restoration of an organ or tissue or new growth by an organism of organs and tissues that have been lost, removed, or injured. Regeneration can occur through several mechanisms, including but not limited to regrowth, restructuring, and cellular repopulation. Regrowth refers to growing, developing, and gradually increasing in size, number, value, or strength. Restructuring refers to a change in cell type, organ or tissue shape, pattern, cell type, connectivity, or arrangement than was originally present. Cellular repopulation refers to development of an area starting from a group of cells that can be exogenous from another part of the body or introduced in medical or experimental procedures to cause a specific effect of growth in a damaged area. Any of the processes or regeneration can be brought about or enhanced via introduction of synthetics, exogenous materials mimicking internal, natural, agents, and can be brought about by pharmacological reagents including agonists or antagonists to enhance regeneration.

Treatment position refers to a position such as, but not limited to, a position from the skin surface of a patient to the most distal edge of a target region where the energy delivery device is capable of treatment of a tissue to cause irreversible electroporation. Various treatment positions include placement such that irreversible electroporation occurs in a target region with at least a portion of the energy delivery device placed within the target region; also, an additional position includes positioning at least a portion of the energy delivery device such that it touches the surface of the target region. Yet other treatment positions include positioning at least a portion of the energy delivery device such that it is adjacent, or near to the target region.

Referring now to FIG. 1A, one embodiment of an energy delivery device 1 is depicted in FIG. 1A as a bipolar probe, including the handle 3 of the bipolar probe, shaft 5 (shown here as a needle 5), a proximal electrode 7, a distal electrode 11, an electrode spacer 9, a tip 13 of the bipolar probe shown here in this embodiment as a three faced trocar tip, and a probe connector 15 of the bipolar probe. Hereafter, the term energy delivery device and probe will be used interchangeably, with specific information regarding the type of probe being added to clarify monopolar, bipolar, and array types of energy delivery devices. The probe is coupled to a nonthermal power source 17, which has a positive and negative connector 19 for the bipolar probe 1. It is understood that in various embodiments the energy delivery device may be in the form of probes that are multiple monopolar, bipolar, or array formations; in embodiments using a bipolar as well as the array approach, there can be more than 1 anode or cathode on a given needle 5 of a probe. The monopolar embodiment can be used with two monopolar probes, one monopolar probe and a pad as known in the art, or in combination with bipolar probes or arrays of probes. Each of monopolar, bipolar, and array devices can be utilized together. In additional embodiments various portions of the probe are flexible or semi-flexible or articulating. In various embodiments the needle is of various flexibilities and may be articulating. In various embodiments the IRE power source can be a generator or other energy source and can be connected to a catheter that allows flexible entry into a lumen. This allows for utilization of the optimal probe for a given medical procedure.

Still referring to FIG. 1A, FIG. 1A also shows the following: a container 101 having a sealable cap 115 for introducing and removing material, an infusion pump 103, a first material transfer tube 113 between a container 101 and an infusion pump 103, and a second material transfer tube 105 and a third material transfer tube 111 that allow transfer of materials between the infusion pump 103 and the handle 3 of the bipolar probe. The second material transfer tube 105 has an end with a first fitting 107 that allows coupling to a second fitting 109 on one end of the third material transfer tube 111.

The container 101 represents any source of materials for introduction through the energy delivery device. The container can store one or more regenerative materials transiently, long-term, or permanently. The container can be programmable such that it stores materials at various temperatures, and can have or be coupled to a temperature controller to maintain regenerative material at a selected temperature. The container can also have an internal portion that rotates or otherwise changes position so as to ensure materials stay in solution or do not adhere to the bottom or sides surface through gravity and other adhering forces. The container can have multiple regions each containing one or more regenerative materials that can be released singly or in combination to the target region of tissue through the needle 5 of the probe through one or more lumens and one or more couplings. The container can also be programmable regarding pressure or pH levels, and can have internal sensors so as to allow regulation of water volume or viscosity. The container is capable of containing any regenerative materials described herein.

The sealable cap 115 allows for placing material within the container 101 and for removing material from container 101. The cap can comprise; one or more electrical or mechanical pieces that acts as a door to provide for moving of the materials; this can include a door, sealable shaft, rubber or plastic pieces allowing a syringe or container or hand to be placed within the interior of the container to replace or remove materials.

The infusion pump 103 provides for movement of the materials to the energy delivery device. The infusion pump 103 is capable of moving materials including but not limited to liquids, gases, semi-solids, and combinations of materials of various states from gas to liquid to solid. The infusion pump 103 is capable of moving any regenerative materials mentioned in this specification. In one various embodiments the infusion pump 103 moves stem cells. The infusion pump 103 can be programmable directly or remotely through any wireless system known in the art, and can deliver materials at any rate, including from introduction through drips to high pressure release of fluid. The programmable part can provide for regulation of volume or pressure of release. The infusion pump 103 can be powered via battery, or plug in to any wall outlet known in the art, from a generator, or can be powered from a diversion of power to the handle 3 of the probe. The infusion pump 103 can be programmed so as to release multiple regenerative materials. The infusion pump 103 can also be programmed to release one or more regenerative materials at various timepoints or the same or varying volumes.

In various embodiments the infusion pump 103 is capable of being a source for or storing regenerative materials (or both storing and being a source of) and in certain embodiments the infusion pump and container store materials. In various embodiments the infusion pump and container are contained in a unit that is part of the handle 3.

The first material transfer tube 113 allows movement of material between the container 101 and the infusion pump 103. In various embodiments the infusion pump 103 is located on the handle 3 of the probe. In other embodiments the container 101 and the infusion pump 103 are one unit and there is no material transfer tube 113.

The first fitting 107 allows coupling to the second fitting 109 and sealably couples one end of the second material transfer tube 105 to the second fitting 109 located on one end of the third material transfer tube 111 and provides for material movement through the handle 3 toward tissue through the needle 5 of the probe.

The second fitting 109 can couple with the first fitting 107. Second fitting 109 can also couple directly to a syringe or multiple syringes. In various embodiments the container is a syringe or a series of syringes; in various embodiments the second fitting 109 couples directly to the container 101 and in other embodiments there is no infusion pump. In certain embodiments manual power of the syringe plunger provides for movement of materials through the energy delivery device. In various embodiments the syringe is coated with a material on the interior to enhance survival or activity of regenerative material; the syringe can also be shaped or have a diameter such as to limit cellular shear stress.

The material transfer tubes (113, 105, 111) can each be made of any material allowing for transfer of materials. In various embodiments the tubes have coatings that prevent sticking of materials to the walls. In other embodiments the diameter is large enough to minimize shear stress on inserted cells.

FIG. 1B depicts an enlarged side-view of the distal portion of the needle of the bipolar probe. Shown are the proximal 7 and distal 11 electrodes separated by the electrode spacer 9, as well as a tip 13 of the bipolar probe shown here in this embodiment as a three faced trocar tip. In addition, a channel 21 is illustrated which in one embodiment is hollow and allows for the movement of materials including liquids. The needle is any shaft capable of delivery of materials through the probe that is also capable of delivery of voltage. In certain embodiments the needle is capable of or adapted for movement of regenerative material.

Though FIG. 1B depicts an example embodiment with a channel shown as a single opening at the end of the probe, this is only one embodiment of many possible. The single channel could be centered within the needle of the probe, or could be placed nearer to one edge, and the end of the opening could be completely open or could be partially or fully covered with a solid, permeable, or semi-permeable covering, with or without micropores that allow for efficient release of regenerative materials for a given tissue. In additional embodiments there are a series of channels allowing for simultaneous or non-simultaneous, single or multiple releases of regenerative materials.

In certain embodiments the needle has a series of apertures at various points along its length so as to allow release of fluids and small particles. The release in all stated examples herein can be either active or passive release of regenerative materials. In addition, the IRE power source can be coupled to a catheter that can be used for ablation as well as for release of regenerative materials, and in various embodiments the catheter has a series of apertures along its length to release regenerative materials actively or passively.

Though FIGS. 1A and 1B show a channel for release of regenerative material from the needle of the probe, this is but one example of one configuration. The probe can be designed so as to be loaded with regenerative materials through one or more openings in the handle or the needle. In one embodiment the opening allows for the loading and releasing of regenerative materials in a straight line from the point of loading to the release point, so as to minimize turbulence and shear stress on any released cells or other materials. In another embodiment, there is a loading where there is an angle of greater than zero degrees from the point of loading to the point of release, such as an embodiment where there is an opening designed to receive materials from a syringe that can be coupled to the handle in a Y-shape.

Though FIG. 1B shows a single channel in a needle of a probe as a release point for regenerative material, the ablation and release of regenerative materials can be performed using an ablation probe singly or in combination with single or multiple catheters, syringes, or additional probes in cases including percutaneous, laparoscopic, and open surgery.

FIG. 1C is an enlarged cross-section of the distal portion of the needle of the bipolar probe from Section A-A of FIG. 1B. Depicted are the proximal 7 and distal 11 electrodes which are separated by a portion of insulative material reaching the outer surface of the needle and which is the electrode spacer 9. Also shown is the channel 21 within the probe, as well as the outer insulation 23 and inner insulation 25. In certain embodiments one or both of the outer and inner insulative materials is composed at least in part of polyester shrink material in single or multiple layers. The channel allows for the passage of materials such as fluids.

The channel can be used to release regenerative materials following ablation. In certain embodiments the channel can also be used to release factors to optimize the environment prior to the introduction of the regenerative materials. Optimizing refers to affecting the treated region in a way that either returns the region to a homeostatic condition or otherwise improves the likelihood, rate, or efficiency of regenerative materials in causing of effecting regeneration. This could involve active or passive rebalancing of tissue levels of materials following ablation, involving singly or in combination adding or altering the levels of water, ions, or factors such as hormones, paracrine agents and paracrine-type agents, and pharmacological mediators including vasoreactive elements. The introduced factors can be natural or synthetic and in certain cases can involve the introduction of a layer of cells. Optimization can be brought about through the introduction of factors.

In certain embodiments, either before or after the release of the regenerative materials (which may be released as a solution) or in combination or as part of the release of the regenerative solution, factors may be released singly or in combination including growth factors (to, in some cases, increase the growth of cells or in some cases to increase the growth rate of certain cells or all cells and in other cases to prevent the growth of certain cell types that may inhibit regeneration or lead to aberrant or undesirable regeneration) such as VEGF, cytokines, and anti-inflammatory agents. In certain embodiments these factors may increase the chance of successful regeneration. In certain embodiments, ion levels are altered singly or in combination, such as sodium, potassium, magnesium and calcium levels. In other embodiments the factors or ions are released with one or multiple cell types before, after, or in a simultaneous release with the cells to advance regeneration. In certain embodiments the regenerative material includes cells and factors that aim to restore tissue, membranes, or matrices. This can involve direct application of a variety of regenerative materials released singly or in combination, in whole, in part, or precursors of DNA, RNA, proteins, carbohydrates, sugars, lipids, enzymes, proteases, steroids, amino acids, purine bases, pyrimidine bases, deoxyribose sugar, ribose sugar, nucleosides, adenosinetriphosphate, and adenosine biphosphate, polysaccharides, proteoglycans, hyaluronic acid, collagen, fibronectin, elastin, laminin, and integrins. The regenerative material could also include singly or in combination smooth muscle cells, eplithelial cells, endothelial cells, liver cells, lung cells, pancreatic cells, and bone cells.

Figure 2A:
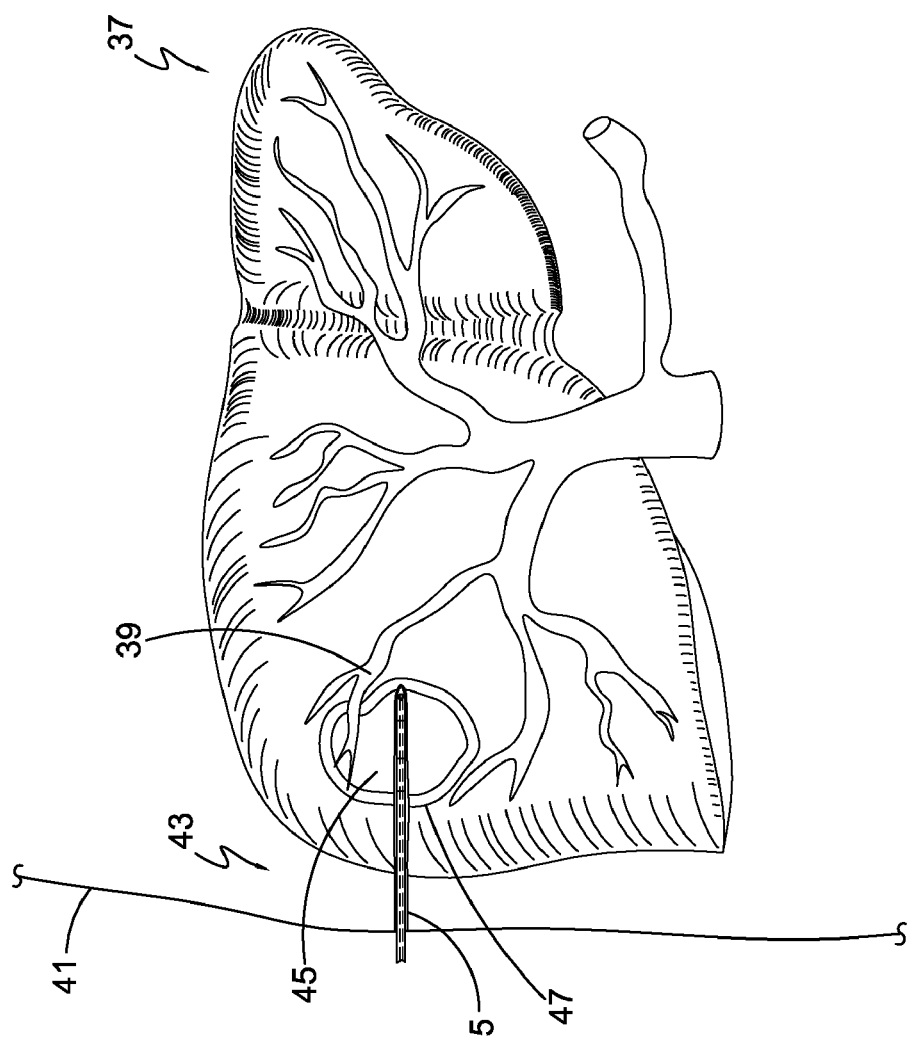
FIG. 2A depicts a cross-sectional view of a liver with a target region of tissue within the liver, where a needle of a bipolar probe coupled to an IRE power source has been inserted into the target region of tissue within the liver and where the safety zone of ablation surrounding the target region in the liver as well as interstitial space and a skin surface are shown for perspective.

FIG. 2A illustrates the ablation and regeneration concerning a target region in a liver. Specifically, this depicts a cross-sectional view of a liver 37 with a target region of tissue 45 within the liver, where a needle 5 of a bipolar probe coupled to an IRE power source has been inserted into the target region 45 of tissue within the liver. There is a safety zone of ablation 47 surrounding the target region in the liver, though it is a very small layer and is shown here not necessarily to scale for ease of visualization. In addition, interstitial space 43 and a skin surface 41 outside the liver are shown for perspective.

Figure 2B:
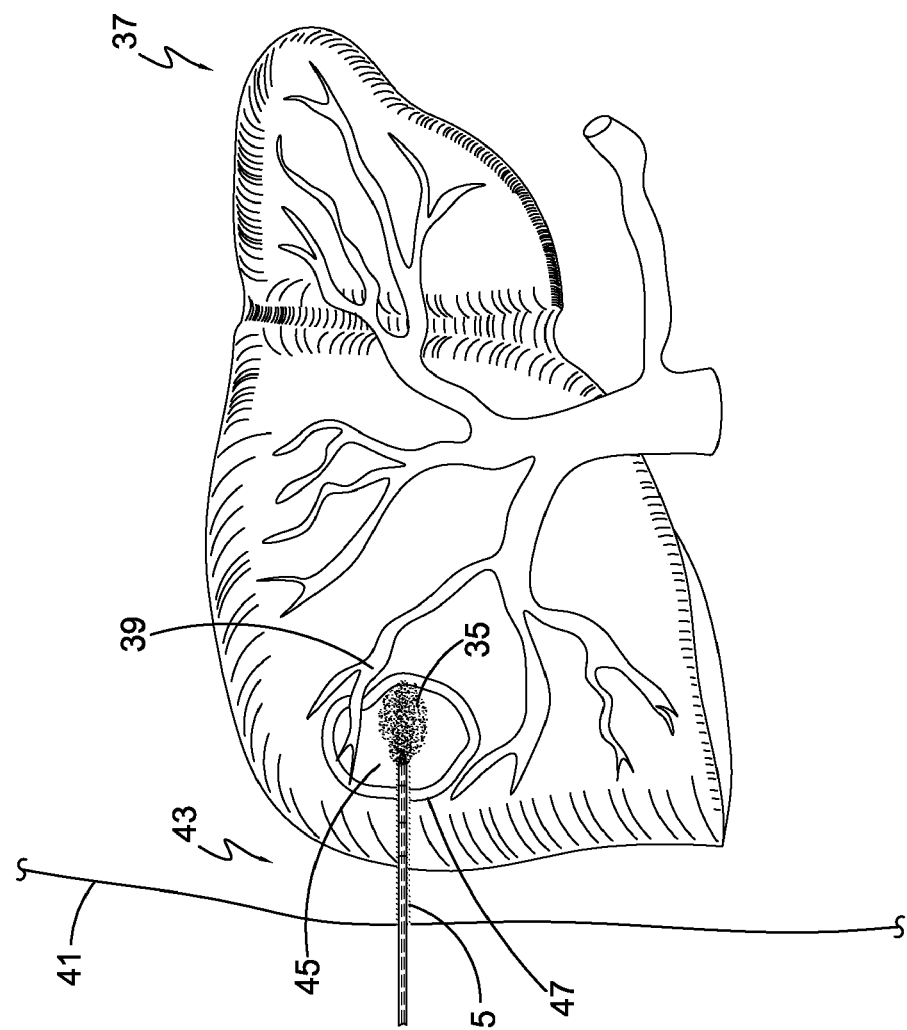
FIG. 2B is a cross-sectional view of the liver from FIG. 2A at a later time point, where IRE ablation has been performed, and regenerative materials are being released into the region that has been ablated with IRE energy within the liver through a channel in the needle of the bipolar probe.

FIG. 2B depicts the liver from FIG. 2A at a later time point once ablation has been performed. Structures shown include a liver 37, blood vessels 39 within the liver, a target region of tissue 45 within a liver, and a safety zone of ablation 47 surrounding the target region. Also shown is a needle of a bipolar probe 5, and regenerative materials 35 released from the probe into the previously ablated region.

The use of regenerative materials released in FIG. 2B depict regeneration in relation to a liver, though this is only one example among various applications of this technology. In various embodiments, release of regenerative materials involves ablation of target regions that can include or be within digestive, skeletal, muscular, nervous, endocrine, circulatory, reproductive, integumentary, lymphatic, urinary, and soft tissue. The targets may also include benign or malignant cancerous, neoplastic, preneoplastic, or tumors as stand-alone targets or targets found within another tissue (such as an organ or organ system).

In various embodiments released regenerative materials include stem cells that range from totipotent, to pluripotent, to multipotent, and to unipotent. In certain embodiments the stem cells utilized include cell lines currently available commercially. These stem cell lines may be human or other animal cell lines, which may or may not be genetically altered, or may be chimeras or may be released with factors enhancing regeneration obtained or derived from humans or nonhuman animals or both. For example, in certain embodiments released regenerative materials include a cell line available from ATCC (Manassas, Va.). An example embodiment would utilize a cell line with ATCC number SCRC-2002 with designation hESC BG01V of the cell type Embryonic Stem Cell. Other embodiments would include cell lines from any of the following: BresaGen, Inc. (Cell lines with provider codes such as Hesbgn-01, Hesbgn-02, Hesbgn-03, Hesbgn-04), Cellartis AB (Cell lines with provider codes such as Sahlg-renska 1, Sahlgrenska 2), ES Cell International (Cell lines with provider codes such as HES-1, HES-2, HES-3, HES-4, HES-5, HES-6), Technion-Israel Institute of Technology (Cell lines with provider codes such as I 3, I 3.2, I 3.3, I 4, I 6, I 6.2, J 3, J 3.2), University of California at San Francisco (Cell lines with provider codes such as HSF-1, HSF-6), as well as the Wisconsin Alumni Research Foundation (Cell lines with provider codes such as H1, H7, H9, H13, H14). Additional embodiments utilize cell lines from the National Stem Cell Bank. Yet an additional embodiment utilizes cells with at least one of the genetic code for or expressed marker of SSEA-1.

Figure 3A:
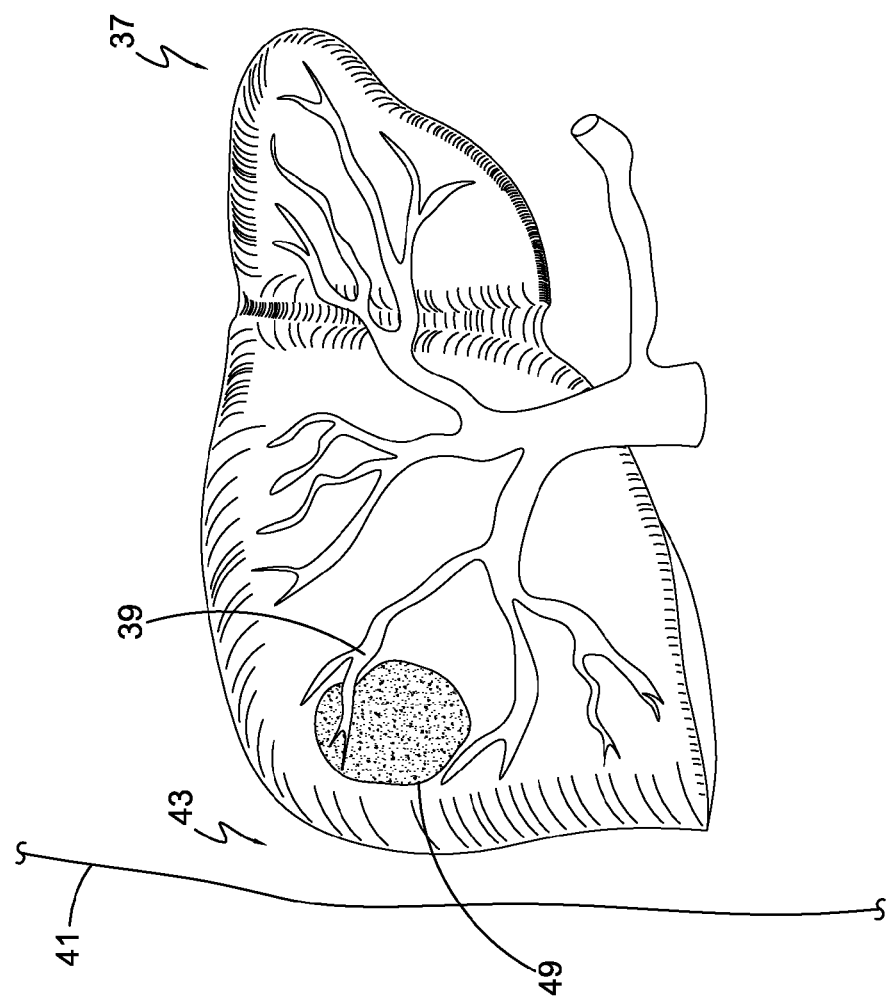
FIG. 3A is a cross-sectional view of the liver from FIG. 2B at a later time point, where the released regenerative materials have settled within the total region that was ablated with IRE energy within the liver at the start of the regenerative process.

FIG. 3A is a cross-sectional view of the liver from FIG. 2B at a later time point, where the released regenerative materials have settled within the total region that was ablated 49 with IRE energy within the liver at the start of the regenerative process. For perspective, FIG. 3A shows the liver 37 with vessels 39, the total region ablated 49, as well as interstitial space 43, and a skin surface 41 surrounding the liver.

Figure 3B:
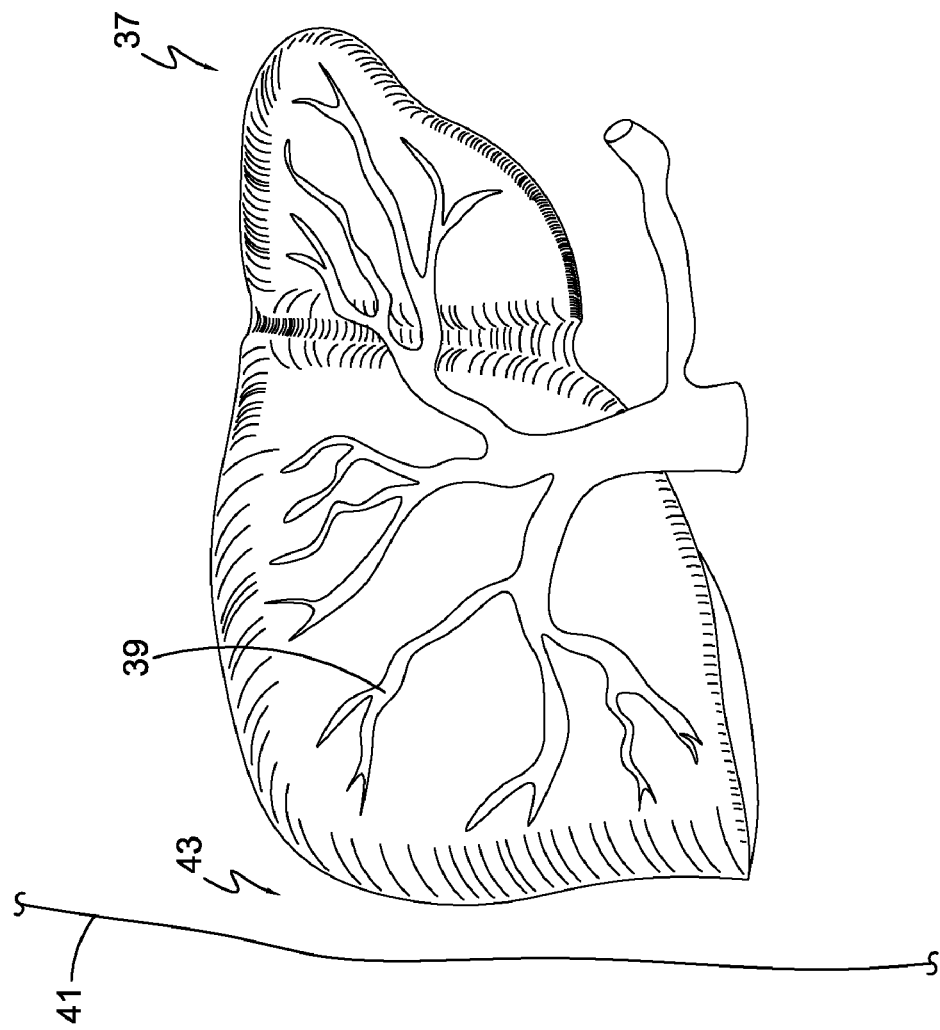
FIG. 3B is a cross-sectional view of the liver from 3A at a later time point, when the regenerative process has been completed and the liver has been restored.

FIG. 3B is a cross-sectional view of the liver from 3A at a later time point, when the regenerative process has been completed and the liver has been restored. This illustrates the liver 37, vessel 39, the interstitial space 43 outside the liver, and a skin surface 41.

Figure 4A:
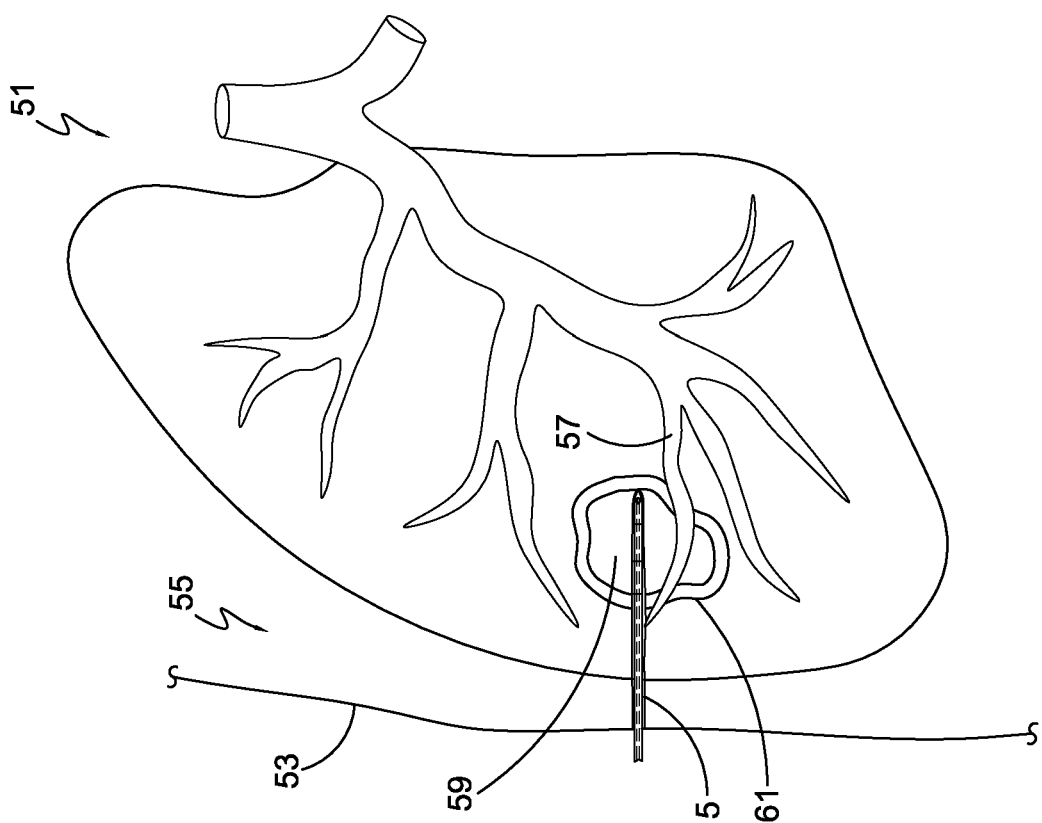
FIG. 4A depicts a cross-sectional view of a lung with a target region of tissue within the lung, where a needle of a bipolar probe coupled to an IRE power source has been inserted into the target region of tissue within the lung and where the safety zone of ablation surrounding the target region in the lung as well as interstitial space and a skin surface are shown for perspective.

Referring now to FIG. 4A, this illustrates the ablation and regeneration concerning a target region in a lung. Specifically, FIG. 4A depicts a cross-sectional view of a lung 51 with a target region 59 of tissue within the lung, where a needle 5 of a bipolar probe coupled to an IRE power source has been inserted into the target region of tissue 59 within the lung and a safety zone of ablation 61 surrounding the target region in the lung. Also shown for perspective are branches of airways 57 as well as interstitial space 55 and a skin surface 53.

Figure 4B:
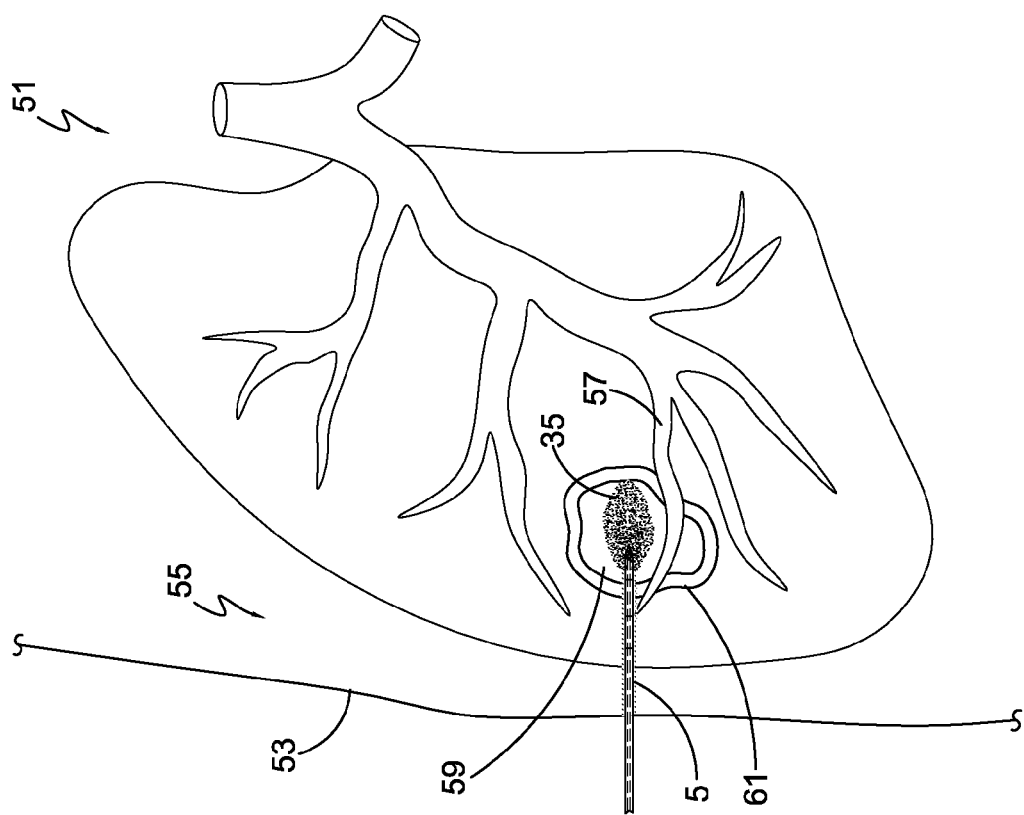
FIG. 4B is a cross-sectional view of the lung from FIG. 4A at a later time point, where IRE ablation has been performed, and regenerative materials are being released into the region that has been ablated with IRE energy within the lung through a channel in the needle of the bipolar probe.

FIG. 4B is a cross-sectional view of the lung from FIG. 4A at a later time point, where IRE ablation has been performed, and regenerative materials are being released into the region that has been ablated with IRE energy within the lung through a channel in the needle of the bipolar probe. Depicted are a lung 51 with a target region 59 of tissue within the lung, where a needle 5 of a bipolar probe coupled to an IRE power source has been inserted into the target region of tissue 59 within the lung and a safety zone of ablation 61 surrounding the target region in the lung is shown. Also shown for perspective are branches of airways 57 as well as interstitial space 55 and a skin surface 53. Also, release of the regenerative materials 35 from a channel in the needle of the bipolar probe is shown.

The use of regenerative materials released in FIG. 4B depict regeneration in relation to a lung, though this is only one example among various applications of this technology. The technology can be applied to release of regenerative materials in any of the ablation targets described in this application.

As previously indicated, in various embodiments of ablation involving the release of regenerative materials, the released materials will include stem cells. However there are various sources of stem cells that are contemplated within this technology. There are varied sources of stem cells, with a variety of methods being developed largely in response to concerns of the use of embryos by scientists in endeavors for developing stem cell lines (which in such a case would be an embryonic stem cell line). There have been significant advances recently due in part to scientists undertaking a search to establish genetically stable stem cells that are long-lived and pluripotent in nature, and that are in essence equivalent to human embryonic stem cells, but which can be established without the destruction of an embryo. The results have been an increased number of sources of stem cells and methods of producing the cells and cell lines. To this point, there are several methods and sources of stem cells.

In certain embodiments, released regenerative materials include cells of variable potencies that have been dedifferentiated. In other embodiments the cells used involve cells dedifferentiated via genetic alterations. In yet another embodiment, the cells used have been dedifferentiated through epigenetic alterations. In yet another embodiment, the cells used have been dedifferentiated through exposure to external factors, ex vivo or in situ or in vitro, or through a combination of these.

Additional embodiments of cells that may be utilized within the regenerative materials released include any or a combination of the following: stem cells derived from dead embryos in what has been termed the Landry-Zucker proposal by those in the art, stem cells derived from an embryo that lead to the destruction of the embryo, stem cells from living human embryos without harming the developmental capabilities of such embryos, and stem cells isolated or obtained through use of somatic cell nuclear transfer (SCNT). Additional embodiments include use of stem cells derived from a constructed biological artifact in a modification of SCNT method of removing an egg's nucleus and replacing it with a somatic cell nucleus in what is known as altered nuclear transfer (ANT), thereby altering the somatic cell nucleus before transfer so that the result is an artifact without essential attributes of a human embryo. Still additional embodiments involve the use of multipotent or pluripotent adult human stem cells. Additionally, variations in stem cell use may involve animal cells of various potencies for release as part of the regenerative materials. In certain embodiments, cells will be isolated from a given individual for reintroduction as part of the regenerative material into that same individual.

Additionally, in certain embodiments cells or factors to be utilized as part of or in conjunction with the release of regeneration materials include cells or factors isolated using one or more of one of magnetic beads, optical sensors, electric fields, and dielectrophoresis.

Figure 5A:
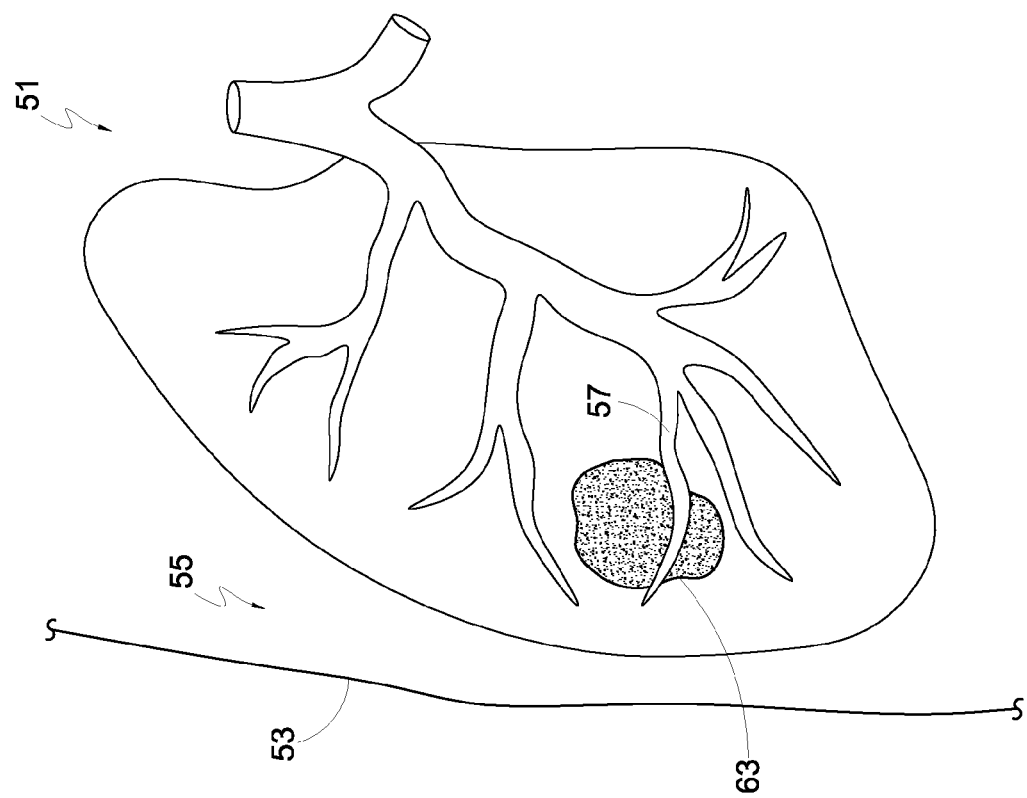
FIG. 5A is a cross-sectional view of a lung from FIG. 4B at a later time point, where the released regenerative materials have settled within the total region that was ablated with IRE energy within the lung at the start of the regenerative process.

FIG. 5A is a cross-sectional view of a lung from FIG. 4B at a later time point, where the released regenerative materials have settled within the total region that was ablated 63 with IRE energy within the lung at the start of the regenerative process. Specifically, FIG. 5A shows a lung 51 with branches of airways 57, as well as the interstitial space 55 and skin surface 53 outside the lung.

Figure 5B:
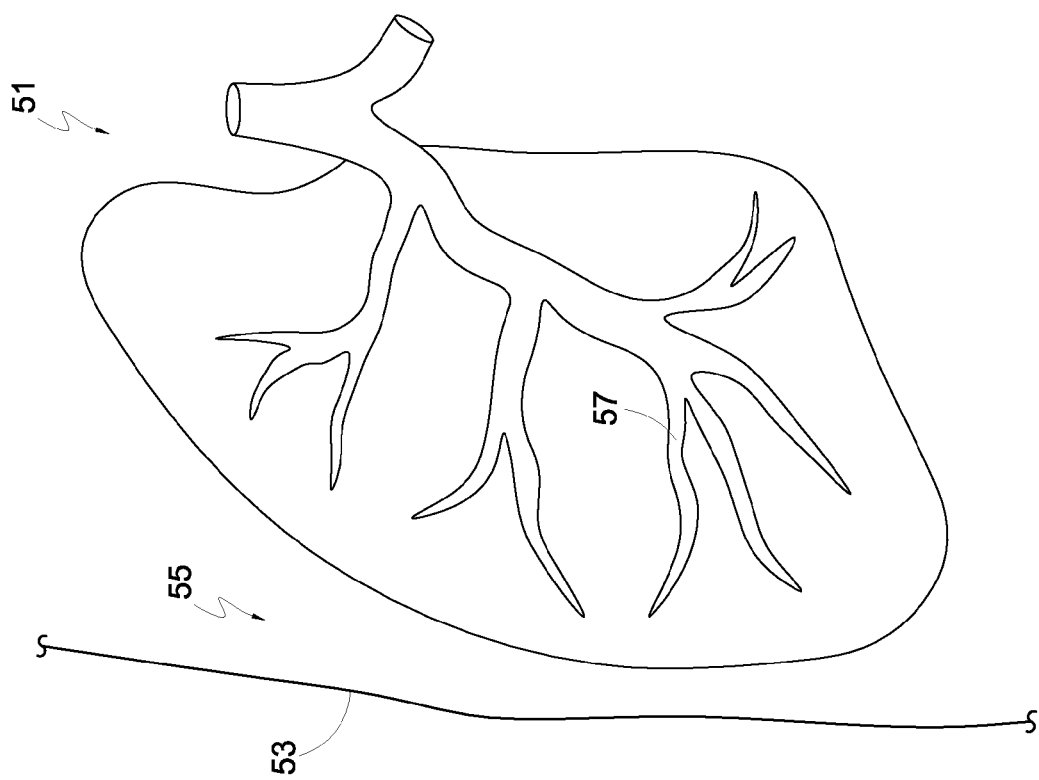
FIG. 5B is a cross-sectional view of the lung from 5A at a later time point, when the regenerative process has been completed and the lung has been restored.

FIG. 5B is a cross-sectional view of the lung from 5A at a later time point, when the regenerative process has been completed and the lung has been restored. Shown is the lung 51, the branches of airways 57, and interstitial space 55 and skin surface 53 outside the lung.

Figure 6:
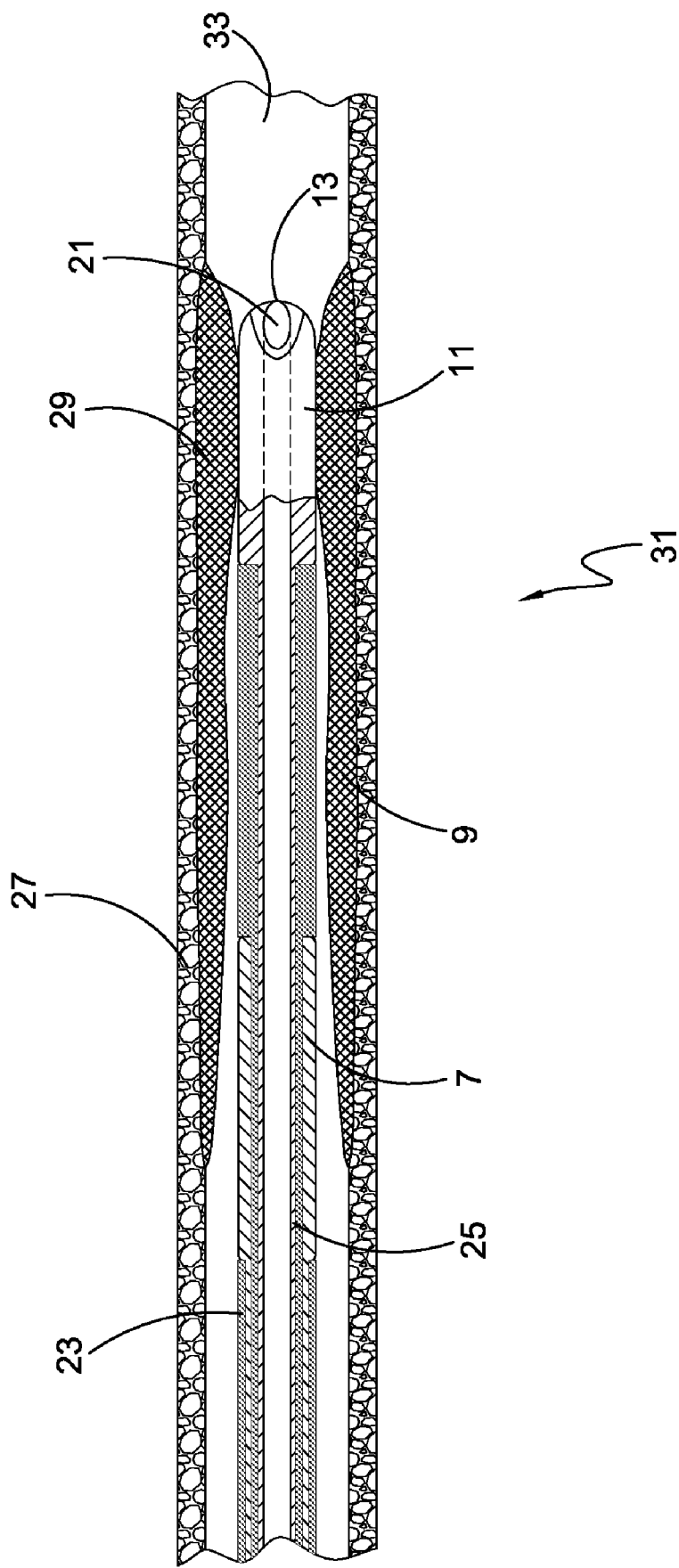
FIG. 6 depicts a cross-sectional view of a blood vessel containing a blockage and the needle of a bipolar probe within the vessel.

Referring now to FIG. 6, depicted is an enlarged cross-sectional view of a portion of the needle of the bipolar probe utilized in the current invention. Shown is a vessel 31, including an endothelial cell layer 27 of a vessel, the lumen 33 of the vessel, and a blockage 29 within the vessel. Depicted within the vessel is the distal portion of a needle of a bipolar probe that could be utilized with IRE ablation. Indicated in the FIG. 6 are the proximal 7 and distal 11 electrodes separated by the electrode spacer 9. Also shown is the channel 21 within the probe, as well as outer insulation 23 and inner insulation 25. In this embodiment the tip 13 of the probe is shown to have a rounded or curved or dulled ending to ensure less damage to the vessel. In conceived embodiments the end could be shard or dull or rounded or curved or padded to ensure proper treatment depending on the specific characteristics of the target region.

Figure 7A:
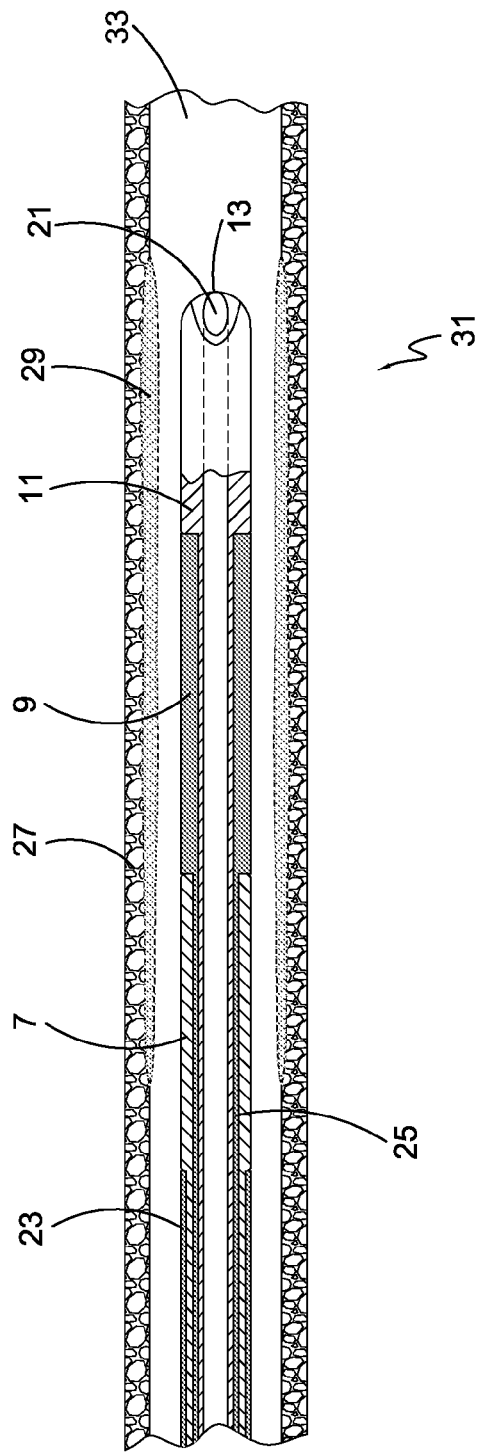
FIG. 7A illustrates a cross-sectional view of a blood vessel immediately after ablation of a blockage by IRE treatment using a bipolar probe shown within the vessel.

FIG. 7A illustrates a cross-sectional view of a blood vessel 31 immediately after ablation of a blockage 29 by IRE treatment using a bipolar probe shown within the vessel. FIG. 7A represents a later time point of the image shown in FIG. 6, where the blockage 29 has been ablated and the reduced material remaining will be resorbed and removed by normal physiological processes within the vessel of the patient. Also indicated are the endothelial cell layer of a vessel 27 and the lumen of the vessel 33. Depicted within the vessel is the distal portion of a needle of a bipolar probe. Indicated in the FIG. 7A are the proximal 7 and distal 11 electrodes separated by the electrode spacer 9. Also shown is the channel 21 within the probe, as well as outer insulation 23 and inner insulation 25, as well as the tip 13 of the probe.

Though a bipolar probe is shown in FIG. 7A for ablation purposes in this particular embodiment within this vessel, there are embodiments involving monopolar probes with various applications in various tissues including but not limited to applications within a vessel (including applications in any regions indicated in this application such as example embodiments including liver as well as lung, or cancerous or tumorous tissues). For example, specifically in relation to the monopolar probe configuration, one embodiment for ablation would include two monopolar probes spaced 10 mm apart, with an exposed length of up to 20 mm. Another embodiment includes a voltage of up to 2000 volts, with pulses of 100 microseconds in length being applied to a target region of tissue. An additional embodiment would involve 90 pulses provided in pulse-trains of 10, with an interval between pulses of 250 milliseconds and a time between pulse-trains of 2 seconds. The total number of pulses and pulse trains in various embodiments varies based on the effectiveness of the treatment for a given tissue. In one embodiment, the ablation zone involves two monopolar probes ablating a zone of approximately 22 mm×18 mm×12 mm, though it is understood that the ablation size and shape varies with placement of the probes and probe types, and that this is an advantage of this invention. Two single probes may also be configured so as to involve other ablation areas, including: ablation of an area of approximately 30 mm×25 mm×17 mm, including exposed electrode lengths of approximately 20 mm and a spacing of 15 mm. Such an embodiment could involve a voltage of 2500 v. It is understood that the ablation size and shape varies with placement of the probes and probe types, and that this is an advantage of this invention.

Specifically in relation to the configuration involving the bipolar probe one embodiment would include a voltage of up to 2700 v. An additional embodiment would involve 90 pulses provided in pulse-trains of 10, with an interval between pulses of 250 milliseconds and a time between pulse-trains of 2 seconds.

In one embodiment, to achieve ablation of the target region of tissue, an IRE generator is used as an IRE power source, utilizing a standard wall outlet of 110 volts (v) or 230 v with a manually adjustable power supply depending on voltage. In another embodiment the generator would have a minimum voltage of 100 v to 3000 v and be adjustable at 100 v intervals. In still another embodiment the ablation pulse applied would be between 20 and 100 microseconds in length, and be adjustable at 10 microsecond intervals. A preferred embodiment would include a generator programmable so as to operate between 2 and 50 amps, with test ranges involving even a lower maximum when appropriate. A preferable embodiment of an IRE generator would include 2 to 6 positive and negative connectors, though it is understood that this is simply a preferred embodiment and that the invention would pertain to additional embodiments understood in the art and necessary for optimal configurations for ablation.

IRE ablation can be performed with variations described in the following reference previously incorporated by reference: U.S. Patent Application Publication Number US 2007/0043345A1, "Tissue Ablation with Irreversible Electroporation," application Ser. No. 10/571,162. Certain embodiments involve pulses between 5 microseconds and 62,000 milliseconds, while others involve pulses of 75 microseconds to 20,000 milliseconds. In certain embodiments electrodes are spaced from 100 Volts per centimeter (V/cm) to 7,000 V/cm, while in other embodiments the spacing is 200 to 2000 V/cm as well as from 300 V/cm to 1000 V/cm. The number of pulses to be used in IRE ablation can vary. In certain embodiments the number of pulses is from 1 to 15 pulses. In other embodiments, groups of 1 to 15 pulses (here groups of pulses are also called pulse-trains) are applied in succession following a gap of time. In certain embodiments the gap of time between groups of pulses is 0.5 second to 10 seconds. Pulses can be delivered using probes, needles, and electrodes each of varying lengths suitable for use in percutaneous, laparoscopic, and open surgical procedures. Electrodes can be made of various materials known in the art and be of different sizes and shapes and be spaced at various distances from one another. Specific embodiments can be square, oval, rectangular, circular or irregular. Certain embodiments have the distance between two electrodes from 0.5 to 10 centimenters (cm), while others have from 1 to 5 cm, and yet others embodiments have from 2-3 cm. The electrode surface area can vary, and in specific embodiments the electrodes are from 0.1 to 5 square cm, and in others, from 1 to 2 square cm. The embodiments described are simply certain embodiments and are not a complete description of embodiments.

Figure 7B:
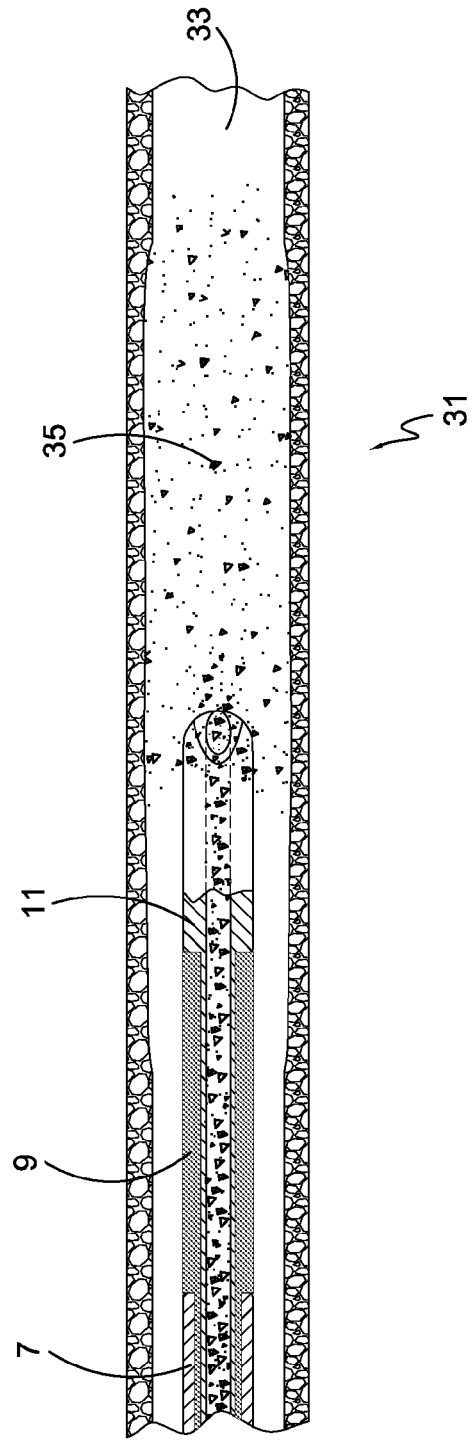
FIG. 7B illustrates a cross-sectional view of a blood vessel, at a later time point from FIG. 7A, after ablation of a blockage by IRE treatment using a bipolar probe shown within the vessel, where regenerative materials are being released from a channel in the bipolar probe.

FIG. 7B is a later time point of the images seen in FIG. 7A, including a vessel 31 with a lumen 33, and inside the lumen is the distal portion of a needle of a bipolar probe. The proximal 7 and distal 11 electrodes can be seen, as well as the electrode spacer 9. In addition, FIG. 7B illustrates introduction of regenerative materials 35 into the lumen 33 of the vessel at the site of ablation.

In one embodiment the regenerative materials released into the vessel contain precursor cells capable of developing into a given cell type intended for reintroduction or regrowth or population development or redevelopment in cell number or size. Though various embodiments are described here in relation to ablation and in relation to a vessel as an example, such precursor cells could be utilized via any of the tissue types described for targeting in this writing for the same purpose, for any of various regenerative treatments.

In various embodiments the introduced regenerative materials include endothelial cell precursors or precursors from tissues such as but not limited to blood, bone, or muscle (such as satellite cells as well as mesodermal-stromal cells). There are tissue specific stem cells at various places in the body, including satellite cells in muscle (as has been described in Rando T. A. *Stem Cells, Ageing and the Quest for Immortality*. Nature. Vol. 441(7097):1080-1086 (2006) incorporated by reference) and mesodermal stromal cells (MSCs) that are bone-marrow derived (Described in the following reference hereby incorporated by reference: Hermann A., Maisel M., Storch A., *Epigenetic Conversion of Human Adult Bone Mesodermal Stromal Cells into Neuroectodermal Cell Types for Replacement Therapy of Neurodegenerative Disorders*, 6(7) Expert Opinion on Biological Therapy 6(7):653 (2006))

In other embodiments the introduced regenerative material includes one or more isolated cells containing the gene for, capable of expressing, expressing, or differentially expressing singly or in combination VE Cadherin (CD144), Von-Willibrand Factor, thrombomodulin (CD141), PAL-E, PECAM-1 (CD31), CD146, VEGF Receptor-1 (FLT-1), VEGF Receptor-2, VEGF Receptor-3, TIE-1 (C-Terminus), TIE-1 (N-terminus), TIE-2, CD34, ICAM-1 (CD54), P-Selectin (CD62P), and Anti-Endoglin (CD105). Embodiments include cells with various homologues of the listed materials as well as other known RNA splice variations and isoforms.

In still additional embodiments the introduced regenerative material includes one or more of cells containing the gene for, capable of expressing, expressing, or differentially expressing singly or in combination neural cell adhesion molecule (N-CAM), fetal antigen 1 (FA1), Pax7, Asb5, IgSF4, Hoxc10, Myf5, Neuritin, Klra18, as well as MyoD target genes (such as Pw1, Dapk2, Sytl2, and NLRR1). Embodiments include cells with various homologues of the listed materials as well as other known RNA splice variations and isoforms.

In still additional embodiments the introduced regenerative material includes one or more of cells containing the gene for, capable of expressing, or expressing, or differentially expressing singly or in combination STRO-1, HOP-26 (CD63), CD49a and SB-10 (CD166), CD13, CD29, CD44, CD73, CD90, Cadherin-11, Calretinin, CD10, CD117, Desmin, Endoglyx-1, Endosialin (TEM1, CD248), Fibroblast-Activation Protein (FAP), Laminin gamma2 chain, Neural Ganglioside GD2, Nucleostemin, Snep (stromal nidogen extracellular matrix protein), and Tenascin. Embodiments include cells with various homologues of the listed materials as well as other known RNA splice variations and isoforms.

In still additional embodiments the introduced regenerative material includes one or more of cells containing the gene for, capable of expressing, expressing, or differentially expressing singly or in combination known pluripotent stem cell markers as: Alkaline Phosphatase, Alfa-fetoprotein (AFP), Bone-Morphogenic Protein-4, Brachyury, Cluster Designation 30 (CD30), Cripto (TDGF-1), GATA-4 gene, GCTM-2, genesis, Germ Nuclear Factor, Hepatocyte Nuclear Factor-4 (HNF-4), Nestin, Neuronal Cell Adhesion Molecule (N-CAM), Oct-4, Pax-6, Stage Specific Embryonic Antigen-3 (SSEA-3), Stage Specific Embryonic Antigen-3 (SSEA-4), Stem Cell Factor (SCFor C-Kit Ligand), Telomerase, TRA-1-60, TRA-1-81, and Vimentin.

Introduced regenerative materials include in certain embodiments single or multiple infusions or injections that include sources of materials from autogeneic, isogeneic, allogeneic, and xenogeneic sources, and can include of one or more of cell types from one or more species such as mouse, rat, guinea pig, hamster, rabbit, dog, cow, as well as horse. Additional embodiments include additional mammals that are known in the art and which are routinely used for isolation of cellular tissue for the development of cell lines and for uses in research and medical procedures.

Figure 8:
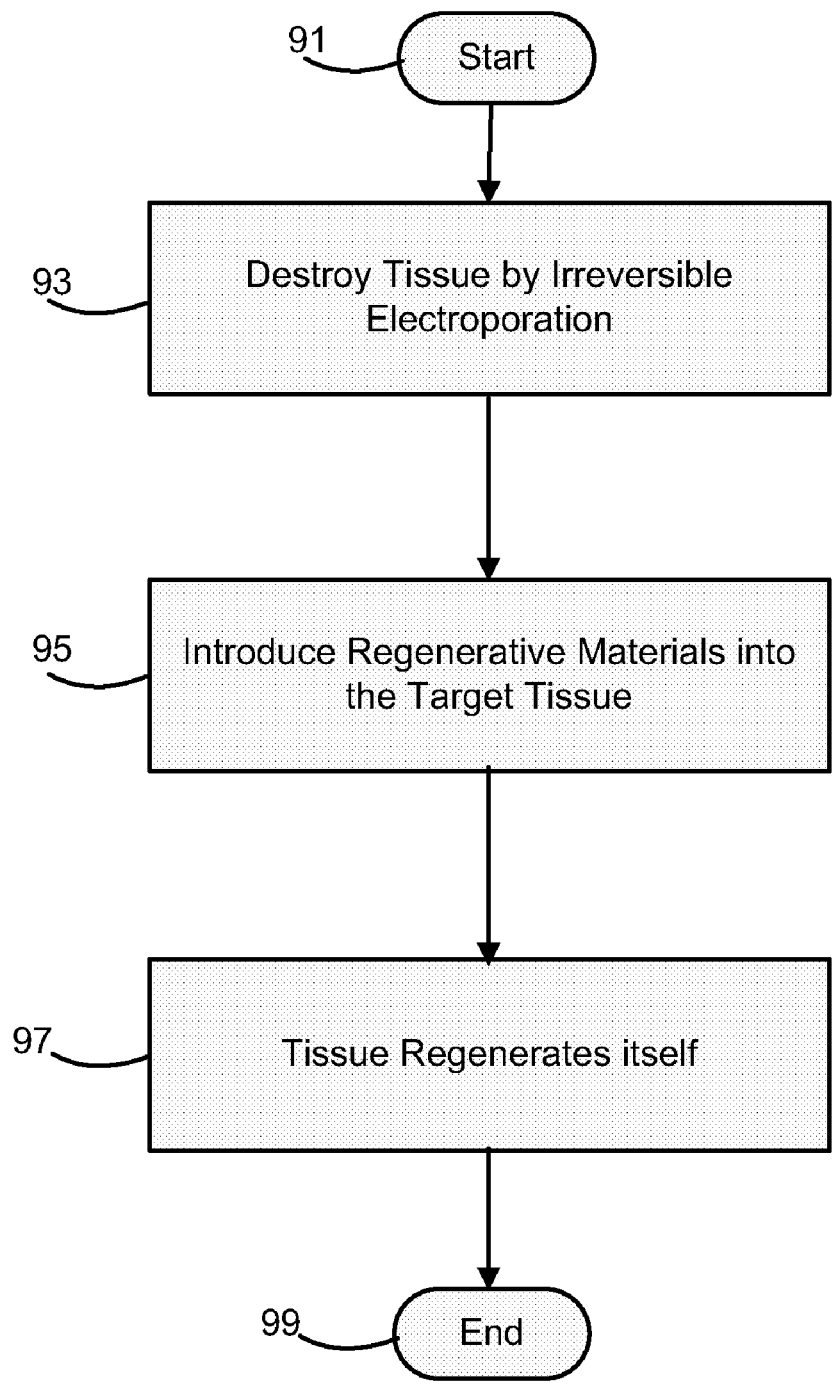
FIG. 8 depicts a flowchart showing a method of ablating a target region and inducing tissue regeneration.

FIG. 8 depicts a flowchart showing a method of ablating a target region and inducing tissue regeneration. At the start 91 of the method tissue is destroyed by irreversible electroporation 93. Regenerative materials are introduced into the area of the target tissue 95, the tissue regenerates itself 97 and the ablation and regeneration comes to an end 99.

Figure 9:
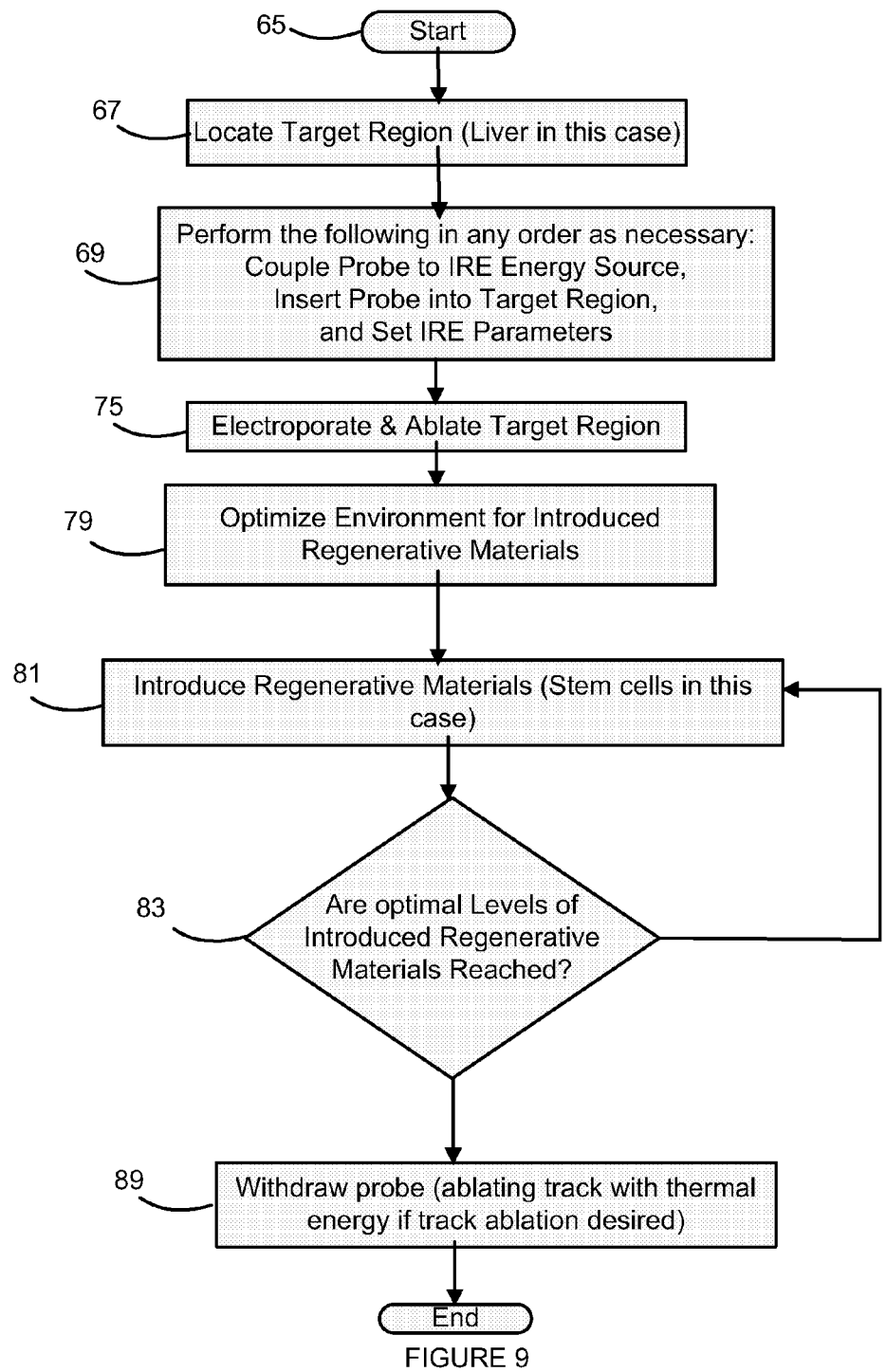
FIG. 9 depicts a flowchart showing a method of ablating a target region within a tissue such as a liver, as well as the introduction of materials capable of inducing tissue regeneration such as a regenerative solution that contained stem cells.

FIG. 9 depicts a flowchart showing a method of ablating a target region within a tissue such as a liver, as well as the introduction of materials capable of inducing tissue regeneration such as a regenerative solution that contained stem cells. At the start 65 of the method the target region is located 67. Though in this shown embodiment a tumor is indicated as the target region within a liver, this is only one example and various embodiments may include any herein described target region. In any order as necessary, the probe is coupled to the IRE power source, the probe is inserted into the target region, and IRE parameters are set 69. IRE electroporation and ablation of the target region is undertaken 75. The environment at the site of ablation is then optimized for the introduction of regenerative materials 79. In various embodiments this may involve actively or passively rebalancing tissue levels of materials by adding water, ions, or factors such as hormones, paracrine-type agents, or pharmacological mediators such as vasoreactive elements. The regenerative materials are added (in this embodiment stem cells) 81 and the question is asked as to whether optimal levels of regenerative materials have been reached 83. If the optimal level has not been reached, additional materials will be added. Once the optimal level of regenerative material has been reached the probe is withdrawn 89, using thermal energy in track ablation in an example embodiment.

In various embodiments the effect of irreversible electroporation can be brought about using a power source of Direct Current (DC). In various embodiments one or more power sources can be used so as to effect irreversible electroporation in a target region and singly or in combination also effect radiofrequency ablation, thermal electric heating, and traditional heating methods with electrodes using direct current or alternating current. These combinations of treatment can be used for additional energy output to have an effect on the target region or on a track to be ablated when the probe is withdrawn to ensure no cells are drawn from the target region towards the patient skin surface as well as allowing coagulation when desired to prevent bleeding.

There exists a need in the art for a method and apparatus that advances regeneration following tissue ablation and that can be used in a wide variety of treatments for a variety of conditions. This method and apparatus provides the significant advantages of allowing for a nonthermal, focal ablation with tissue sparing providing a foundation for which regenerative materials can be most effective. The method of utilization of nonthermal IRE ablation of target regions of tissue and the introduction of regenerative materials may be used in conjunction with additional methods and devices and for the benefit of the patient.

What is claimed is:

1. A method for treating a target region of tissue, comprising:
   providing at least one energy delivery device, wherein the at least one energy delivery device is connectable to a power source, and wherein the at least one energy delivery device comprises:
      a shaft capable of being positioned within the target region of tissue; the shaft having a lumen adapted to receive at least one regenerative material for insertion into the target region of tissue; and
      at least one electrode-positioned on the shaft and adapted to deliver electrical pulses to the target region of tissue in an amount sufficient to irreversibly electroporate the target region of tissue;
   positioning the at least one energy delivery device in a treatment position;
   applying power from the power source to said target region of tissue to irreversibly electroporate at least a portion of the target region of tissue;
   ablating at least a portion of said target region of tissue; and
   introducing the at least one regenerative material into the target region of tissue after the step of ablating.

2. The method of claim 1, wherein the step of positioning includes placing at least a portion of the energy delivery device on a surface of the target region of tissue.

3. The method of claim 1, wherein the step of positioning includes advancing at least a portion of the at least one energy delivery device into the target region of tissue.

4. The method of claim 1 wherein the step of introducing the at least one regenerative material includes releasing the at least one regenerative material through the at least one energy delivery device.

5. The method of claim 1, wherein the at least one energy delivery device involves at least one of a monopolar electrode, bipolar electrode, and an array of electrodes.

6. The method of claim 1, further comprising applying the method as at least part of a medical procedure that involves at least one of a percutaneous, a laparoscopic, and an open surgery.

7. The method of claim 1, wherein prior to the step of introducing the at least one regenerative material, the method further comprises releasing at least one factor to optimize the target region of tissue.

8. The method of claim 7, wherein the factor is at least one of water, ions, hormones, paracrine agents, pharmacological mediators, and vasoreactive elements.

9. The method of claim 1, wherein the at least one regenerative material is applied a sufficient number of times to effect at least one of regrowth, restructuring, and cellular repopulation in the target region of tissue.

10. The method of claim 1, wherein the target region of tissue is at least a portion of a tissue selected from the group comprising: digestive, skeletal, muscular, nervous, endocrine, circulatory, reproductive, integumentary, lymphatic, urinary, and soft tissue.

11. The method of claim 1, wherein the target region of tissue is at least one of a vessel, a liver, a lung, a pancreas, and a prostate.

12. The method of claim 1, where the target region of tissue is at least one of benign, malignant, cancerous, neoplastic, preneoplastic, and tumorous tissue.

13. The method of claim 1, wherein the at least one regenerative material includes at least one of totipotent, pluripotent, multipotent, and unipotent cells.

14. The method of claim 1, wherein said at least one regenerative material is at least one of autogeneic, isogeneic, allogeneic, and xenogeneic.

15. The method of claim 1, wherein the at least one regenerative material includes at least a portion of a cell selected from the group comprising: smooth muscle cells, epithelial cells, endothelial cells, adult stem cells, vascular endothelial cell precursor cells, and mesodermal stromal cells.

16. The method of claim 1, wherein the at least one regenerative material includes at least one cell that is the same cell type as the primary cell type of said target region of tissue.

17. The method of claim 1, wherein the at least one regenerative material includes at least a portion of a cell selected from the group comprising: liver, lung, pancreas, and bone.

18. The method of claim 1, wherein the at least one regenerative material includes at least one of VEGF, cytokines, and anti-inflammatory agents, water, ions, hormones, paracrine agents, pharmacological mediators and vasoreactive elements.

19. The method of claim 1, wherein the at least one regenerative material is at least a portion of a molecule selected from the group comprising: DNA, RNA, proteins, carbohydrates, sugars, lipids, enzymes, proteases, and steroid.

20. The method of claim 1, wherein the at least one regenerative material includes at least one of polysaccharides, proteoglycans, hyaluronic acid, collagen, fibronectin, elastin, laminin, and integrins.

21. A method for treating a target region of tissue, comprising:
   providing at least one energy delivery device, wherein the at least one energy delivery device is connectable to a power source, wherein the at least one energy delivery device comprises:
      a shaft capable of being positioned within the target region of tissue, the shaft having a lumen adapted to receive at least one regenerative material for insertion into the target region of tissue; and at least one electrode positioned on the shaft and adapted to deliver electrical pulses to the target region of tissue in an amount sufficient to irreversibly electroporate the target region of tissue;

positioning the at least one energy delivery device in a treatment position;

setting at least one parameter on the power source to provide power to nonthermally irreversibly electroporate the target region of tissue to achieve ablation;

applying power from the power source according to the parameter to the target region of tissue to irreversibly electroporate at least a portion of the target region of tissue;

introducing said at least one regenerative material into the target region of tissue after the step of applying power; and withdrawing said at least one energy delivery device from the target region of tissue after the regenerative material has been introduced into the target region of tissue.

\* \* \* \* \*